United States Patent [19]

Gallo-Torres et al.

[11] 4,117,121

[45] Sep. 26, 1978

[54] METHOD OF INCREASING BILE FLOW AND DECREASING LIPID LEVELS

[75] Inventors: Hugo Gallo-Torres, Livingston; James Guthrie Hamilton, Nutley; Ann Clare Sullivan, Cedar Grove, all of N.J.

[73] Assignee: Hoffmann-La Roche Inc., Nutley, N.J.

[21] Appl. No.: 790,163

[22] Filed: Apr. 22, 1977

[51] Int. Cl.$^2$ ............................................. A61K 31/56
[52] U.S. Cl. .................................. 424/238; 260/397.1
[58] Field of Search ................................ 424/238, 240

[56] References Cited

U.S. PATENT DOCUMENTS

| 3,153,615 | 10/1964 | Bosshardt et al. | 424/238 |
| 3,591,687 | 7/1971 | Bray | 424/238 |
| 3,636,210 | 1/1972 | Howe et al. | 424/238 |
| 3,639,597 | 2/1972 | Hannah | 424/238 |
| 3,852,440 | 12/1974 | Weigand | 424/238 |
| 3,859,437 | 1/1975 | Weigand | 424/238 |

*Primary Examiner*—Elbert L. Roberts
*Attorney, Agent, or Firm*—Samuel L. Welt; George M. Gould

[57] ABSTRACT

The increase of bile flow and the decrease of the levels of lipids such as cholesterol and triglyceride is obtained in biological systems by utilizing specific 3α, 12α dihydroxy cholane derivatives and the non-toxic salts of these derivatives.

23 Claims, No Drawings

METHOD OF INCREASING BILE FLOW AND DECREASING LIPID LEVELS

BRIEF DESCRIPTION OF THE INVENTION

In accordance with this invention, it has been found that by administering to biological systems compounds of the formula:

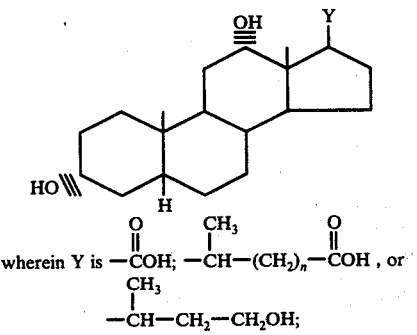

wherein Y is —COH; —CH—(CH$_2$)$_n$—COH, or
—CH—CH$_2$—CH$_2$OH;

and n is an integer of from 0 to 1 or pharmaceutically acceptable salts thereof, increases the bile flow and decreases the lipid levels in the blood of said biological system. More particularly this invention is directed to administering the compound of formula I to mammals to increase the bile flow and decrease the level of lipids such as cholesterol, triglycerides as well as other lipids. By increasing the bile flow while reversing the mechanism whereby excess cholesterol and other lipids such as triglycerides are deposited in the blood stream of various mammals results in a reversal of conditions in mammals such as gall stones by reduction and dissolution of the stone and artherosclerotic plaque formation in blood vessels. Also this property makes the compound of formula I and its pharmaceutically acceptable salts useful for treating obesity.

DETAILED DESCRIPTION

In accordance with this invention it has been found that administering the compound of formula I-A and its pharmaceutically acceptable salts to biological systems increases the bile flow in these biological systems particularly in mammals and decreases the level of lipids such as cholesterol and triglycerides.

Among the compounds of formula I are compounds of the formula

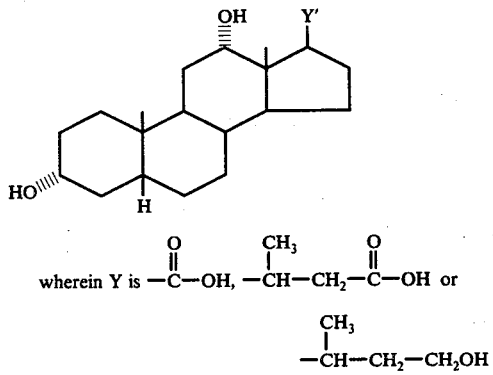

wherein Y is —C—OH, —CH—CH$_2$—C—OH or
—CH—CH$_2$—CH$_2$OH and pharmaceutically acceptable salts thereof which increase the bile flow and decrease the cholesterol and triglyceride levels in biological systems to which they are administered. On the other hand, the compound of the formula:

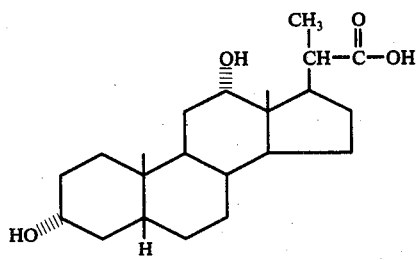

and pharmaceutically acceptable salts thereof increase the bile flow and decrease the triglyceride level in biological systems in which it is administered.

More particularly, it has been found that administration of the compounds of Formula I-A of this invention to hypercholesteremic mammals results in the inhibition of activity of the rate limiting enzyme which controls the rate of cholesterol synthesis in mammals, and thus results in a lowering of the cholesterol and other lipid levels of the hypercholesteremic mammal being treated. In fact, the inhibition of cholesterol synthesis by the practice of this invention results in a decrease of the natural distribution of cholesterol into the plasma and bile of the mammal being treated, and consequently will lead to a reversal of the process whereby excessive cholesterol has been previously deposited resulting in the formation of cholesterol gall stones and artherosclerotic plaque. Thus, administration of the compounds of Formula I-A, in the practice of this invention to hypercholesteremic mammals, will apparently lead to a depletion of excessive cholesterol deposits in the body of said mammal, for example, cholesterol gall stones and artherosclerotic plaque.

In addition to the foregoing, it is now known that substantial amounts of cholesterol synthesized by the liver are converted by the body to desireable bile acids. The rate at which this conversion takes place is controlled by another enzyme, cholesterol-7α-hydroxylase. It has now been discovered that while certain bile acids, notably cholic acid, i.e. 3α, 7α, 12α-trihydroxy-5β-cholanic acid and deoxycholic acid, i.e. 3α, 12α-dihydroxy-5β-cholanic acid, have an adverse effect on the activity of this enzyme, the compounds of this invention have no adverse effect, and in some instances have apparently had an elevating effect on the cholesterol 7α-hydroxylase enzyme. Thus, it has also been found that the compounds of this invention reduce cholesterol by not interfering with and in some instances augmenting the bodys natural process of converting undesired cholesterol into desired bile acids.

The compound of Formula IB, while increasing the flow of bile acids, in the same manner as IA decreases the level of lipids such s triglyceride in biological systems. The compounds of Formula IA and IB decrease the triglyceride levels in systems in which they are administered. Therefore, the compounds of formula IA and IB may be administered to hypertriglyceridemic mammals to inhibit the pancreatic lipase, the enzyme which control the hydrolysis of triglycerides in biological systems such as mammals. Therefore, the administration of the compound of Formula IA and IB to biological systems results in a lowering of the triglyceride absorbed in the system. Therefore, the compounds of this invention, by the inhibition of the pancreatic lipase, significantly reduce the fat caloric absorption in mammals and significantly aid in the treatment of obesity.

The compound of Formula I may be utilized in the form of pharmaceutically acceptable non-toxic basic salts. Preferred salts for this purpose include the alkali metals, e.g., sodium or potassium; the alkaline earth metals, e.g., calcium or complex salts such as ammonium or substituted ammonium salts such as mono-di-or tri-alkyl ammonium salt or a mono, di-or tri-hydroxyalkyl ammonium salt. The compounds of Formula I can be utilized in the form of conventional pharmaceutical preparations; for example, the aforesaid compounds can be mixed with conventional inorganic inert pharmaceutical carriers suitable for parenteral or enteral administration such as, for example, water, gelatin, lactose, starch, magnesium stearate, talc, vegetable oil, gums or the like. They can be administered in conventional pharmaceutical forms, e.g., solid forms, for example, tablets, dragees, capsules, suppositories or the like; or in liquid forms, for example, suspensions or emulsions. Moreover, the pharmaceutical compositions contain compounds of this invention can be subjected to conventional pharmaceutical expedients such as sterilization, and can contain conventional pharmaceutical excipients such as preservatives, stabilizing agents, emulsifying agents, salts for the adjustment of osmotic pressure, or buffers. The composition can also contain other therapeutically active materials.

A suitable pharmaceutical dosage unit can contain from about 16–600 mg. of the compound of Formula I or its salts. Suitable parental dosage regimens in mammals comprise from 1 mg/kg to about 100 mg/kg per day. However, for any particular subject, the specific dosage regimen should be adjusted according to the individual needs and the professional judgement of the person administering or supervising the administration of the aforesaid compounds. It is to be understood that the dosages set forth herein are exemplary only and that they do not, to any extent, limit the scope or practice of this invention.

The biological systems in which the method of the present invention may be practiced includes cell-free enzyme preparations containing pancreatic lipase, tissue homogenates, tissue slices, perfused organs, and intact mammals.

The following examples are illustrative but not limitative of the invention. In the Examples:

Compound A is 3α, 12α-dihydroxy-etiocholane-17β-carboxylic acid.

Compound B is 3α, 12α-dihydroxy-5β-23,24-bisnorcholanic acid.

Compound C is 3α, 12α-dihydroxy-5-β-norcholanic acid.

Compound D is 3α, 12α, 23-trihydroxy-5β-24-norcholane.

EXAMPLE 1

In these studies female albino rats (Charles River), weighing 300 ± 10 g were kept on a Purina chow diet ad libitum until the time of operation. In addition to a thoracic duct cannula, the animals had a double catheterization of the upper part of the common bile duct. This preparation enabled the production of lymph at a constant rate, the infusion of a bile salt, and the simultaneous collection of bile.

All animals received, after operation, a continuous duo denal infusion of sodium taurocholate (Na-TC) in 0.85% NaCl. One day after operation, the rats were given, by stomach intubation, an emulsion containing about 4% triolein, 20 μC of 4-$^{14}$C-cholesterol (Specific Activity 61.7 mC/mM, 159 μC/mg), 2 mg of cholesterol, in addition to protein, carbohydrate, and saline. Both the Na-TC and the cholesterol carrier employed gave a single spot on either thin layer or glass fiber paper chromatograph so no further purification was attempted. The commercial glyceryl trioleate contained a large percentage of di- and monoolein. Triolein was, therefore, purified by passage through a silicic acid column; the final product gave a single spot on either glass fiber paper or thin layer chromatography. The radiocholesterol employed was found to be > 97% pure.

To 4 ml of this emulsion was added 100 mg of either Na-TC (control group) or compounds A through D. This mixture was given orally to the animals.

The sampling of thoracic duct lymph and of bile was divided into two collecting periods, 0–8 and 9–24 h after emulsion administration.

Lymph specimens were lyophilized and the lipids in the residue were extracted with ethanol-isopropyl ether, 2:1 parts by volume, by procedure described in Gallo-Torres, et al; Biophys. Acta, 176 605–615 (1969). An aliquot of the lipid extract was placed on a small piece of glass fiber paper and counted. Another aliquot was used for the separation of cholesterol and its esters by glass fiber paper chromatography.

The effect of compounds A through D derivatives on the appearance of total $^{14}$C-cholesterol in the thoracic duct lymph of rats is summarized in Table I. Of the dose administered to the control animals, $5 \times 10^5$ dpm were recovered in the first 8 h and $3.4 \times 10^6$ dpm in the period of 9–24 h following administration of the emulsion. This higher absorption of cholesterol in the 9–24 h period as compared to the early absorptive period was seen in all experiments, regardless of the nature of the bile acid administered. The tolerance of cholesterol in Table I is the % decrease in the 4-$^{14}$C-cholesterol over the control appearing in the lymph during the specified period.

TABLE I

The Effect of Compounds on the intestinal absorbtion of CHOLESTEROL

| | % decrease of cholesterol Time after Incubation | |
|---|---|---|
| Test Compound | 0–8 hours | 9–24 hours |
| A | 0 | 79 |
| B | 0 | 0 |
| C | 40 | 53 |
| D | 84 | 44 |

The results of the stimulation of bile flow is shown in Table II. In this table the results are expressed as the % increase in bile flow over the control.

TABLE II

EFFECT OF TEST COMPOUNDS ON BILE FLOW

| | % increase of Bile Flow | |
|---|---|---|
| Test Compound | 0–8 hours | 9–24 hours |
| Compound A | +18 | −3 |
| Compound B | +38 | +47 |
| Compound C | +4 | +30 |
| Compound D | +22 | +14 |

EXAMPLE 2

In this Example, Compounds A and B were compared as a bile flow increasing properties with those agents for increasing bile flow such as chenodeoxycholic acid (CDC), deoxycholic acid (DC) and cholic acid (C).

Female rats, weighing approximately 250 g, were fasted overnight prior to surgery; water was allowed ad libitum. The surgical procedures involving cannulation of the upper part of the common bile duct were carried out under Penthrane anesthesia. A catheter placed in the avascular part of the stomach was used for intragastric administration of emulsion; another catheter was placed in the duodenum. After surgery the rats were kept in restraining cages. Intraduodenal infusion of bile (collected previously from donors) was then started at the rate of 0.9 ml/hr. The infusion pressure was kept constant by means of a pump. Hydration was maintained by allowing the animals to drink saline ad libitum.

All rats were allowed ~20 hours to recover from surgery. During this post-surgical period bile was collected in pooled samples of 16-18 hours. Having achieved steady hourly flow, the two samples obtained prior to the actual experiment were collected individually and considered as a control standard for each rat.

Each animal was administered, intragastrically, 100 mg of the test compound dissolved in 3 ml of a standard emulsion used in Example 1.

Bile samples were collected hourly, over a 24-hour period. The volume was measured to the nearest 0.1 ml.

The values in Table III were expressed for the purpose of the analysis, as a percent change from average bile collected in the two hours immediately preceding treatment.

Table III

Comparative Effect of Test Compounds on Bile Flow

| Test Compound | % increase in Bile Flow | | |
|---|---|---|---|
| | 0-12 hours | 13-24 hours | overall 24 hour period |
| C | +161 | -123 | +38 |
| DC | +335 | -116 | +219 |
| CDC | +504 | +9 | +513 |
| Compound A | +286 | +79 | +365 |
| Compound B | +517 | +113 | +630 |

EXAMPLE 3

Dietary long-chain triglycerides must be hydrolyzed by pancreatic lipase in the duodenum before absorption can occur. Compounds which inhibit pancreatic lipase would significantly reduce fat caloric absorption and represent useful antiobesity and hypotriglyceridemic agents.

The capacity of compounds B and C to inhibit rat pancreatic lipase in vitro was investigated.

The ability of compounds to inhibit rat pancreatic lipase is determined by analyzing the nmoles of free fatty acid [oleic acid] released from [$^{14}$C]-triolein. Compounds of B and C are added to an emulsion consisting of: 200,000 dpm $^{14}$C-triolein, 7.5 mg triolein, 0.75 mg sodium taurocholate, 15 mg bovine serum albumin and 0.9 ml 0.2 M tris-HCl - 0.15 M NaCl, pH 8.6, per assay. Water and/or pancreatic lipase is added to make an assay volume of 1.0 ml. The emulsion is incubated for 20 min at 37° C. in a shaking water bath. The reaction is stopped by the addition of isopropanol; $H_2SO_4$ (40:1). The lipids are extracted twice with 3 ml volumes of hexane. The liberated fatty acids are extracted with 2 ml of 0.1 N KOH in 50% methanol. A 1 ml aliquot of the KOH layer is placed in a scintillation vial with 10 ml of 2,5-bis-2- (5-tertiarybutyl benzoxazolyl)thiophene. The radioactivity is determined in a scintillation counter. Data are expressed as nmoles free fatty acid [oleic acid] released.

TABLE IV

INHIBITION OF RAT PANCREATIC LIPASE ACTIVITY

| Test Compound | Pancreatic Lipase Activity $K_i$ (mM) |
|---|---|
| Compound C | 1 |
| Compound B | 14 |

EXAMPLE 4

The ability of compound A to inhibit the absorption of dietary triglyceride in rats is determined by analyzing the rise in serum triglycerides after an oral load of corn oil. To 24 hours fasted rats (6 per group), compound A was administered orally at 1.1 mmoles/kg 15 minutes before a single oral dose of corn oil (20 ml/mg). Blood samples (0.4 ml) were collected from the rat tail 0, 2, 4, 6, 8 and 24 hours after compound administration. Each rat is its own control. Plasma samples were analyzed for triglyceride content by the procedure set forth in Kessler and H. Lederer, Tehnicon Symposium 1965 Automation in Analytical Chemistry Ed. L. Skeggs, published Mediad Inc. N.Y. (1966)pp341. The data in Table V is expressed as mg% change in plasma triglyceride levels compared to zero time control values at each time interval. This change in plasma triglycerides was determined by calculating the difference between the triglyceride level at each time point compared to zero time control level.

Table V

EFFECT OF TEST COMPOUND ON TRIGLYCERIDE ABSORPTION IN VIVO

| Treatment | Change in Plasma Triglyceride Levels (mg%) | | | | |
|---|---|---|---|---|---|
| | 2 hr | 4 hr | 6 hr | 8 hr | 24 hr |
| Control | 35 ± 8 | 98 ± 31 | 161 ± 28 | 391 ± 58 | 130 ± 36 |
| Compound A | 37 ± 9 | 50 ± 13 | 113 ± 34 | 164 ± 40* | 83 ± 11 |

*$p<0.05$

EXAMPLE 5

The procedure of Example 4 was followed except groups of 4 were utilized. Compound B was administered. The results are given in Table V.

Table V

EFFECT OF COMPOUND B ON TRIGLYCERIDE ABSORPTION IN VIVO

| Treatment | Change in Plasma Triglycerides (mg%) | | | | |
|---|---|---|---|---|---|
| | 2 hr | 4 hr | 6 hr | 8 hr | 24 hr |
| Control | 23 | 37 | 65 | 117 | 55 |
| Compound B | -3 | 7 | 15 | 54 | 30 |

EXAMPLE 6

A tablet formulation (Wet granulation) was prepared as follows:

| Item | Ingredient | mg/tablet |
|---|---|---|
| 1. | 3α,12α-dihydroxy-5β-norchonic acid | 100 |
| 2. | Lactose | 147.5 |
| 3. | Pregelatinized starch | 25 |
| 4. | Modified starch | 25 |
| 5. | Corn starch | 25 |
| 6. | Magnesium stearate | 2.5 |
| | Weight of tablet | 325 |

-continued

Procedure
1. Mix items 1,2,3,4 and 5 in a suitable mixer, granulate with water, and dry over night in a suitable oven. Mill through suitable mill.
2. Mix with item 6 and compress on a suitable press.

EXAMPLE 7

A tablet formulation (Wet granulation) was prepared as follows:

| Item | Ingredient | mg/tablet |
|---|---|---|
| 1. | 3α,12α,dihydroxy-5β-norcholanic acid | 100 |
| 2. | Lactose | 98.5 |
| 3. | Polyvinyl pyrrolidone | 15 |
| 4. | Modified starch | 15 |
| 5. | Corn starch | 15 |
| 6. | Magnesium stearate | 1.5 |
|  | Weight of tablet | 245 mg |

Procedure
1) Mix items 1, 2, 4 and 5 in a suitable mixer, granulate with Polyvinyl pyrrolidone and dissolve in water/alcohol. Dry the granulation. Mill the dry granulation through a suitable mill.
2) Add magnesium and compress on a suitable press.

EXAMPLE 8

A tablet was formulated in the same manner as in Example 7 except that the active ingredient was 3α, 12α, -dihydroxy-etiocholane-17-carboxylic acid.

EXAMPLE 9

A tablet was formulated in the same manner as in Example 7 except that the active ingredient was 3α, 12α, 23-trihydroxy-5β-24-norcholane.

EXAMPLE 10

A capsule formulation was prepared as follows:

| Item | Ingredient | mg/capsule |
|---|---|---|
| 1. | 3α,12α-dihydroxy-5 - norcholanic acid | 100 |
| 2. | Lactose | 99 |
| 3. | Corn starch | 20 |
| 4. | Tacl | 5 |
| 5. | Magnesium stearate | 1 |
|  | Fill weight of capsule | 225 |

Procedure
1) Mix items 1, 2 and 3 in a suitable mixer. mill through a suitable mill.
2) Mix the mixture in Step 1 with item 4 and 5 and fill on a suitable machine.

We claim:
1. A method for increasing bile flow and simultaneously reducing lipid levels in mammals comprising administering to mammals a compound of the formula

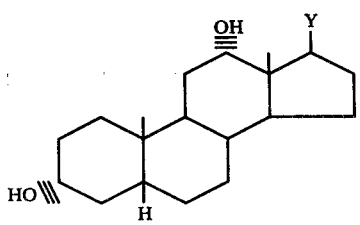

-continued

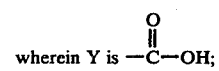

and n is an integer of from 0 to 1; or pharmaceutically acceptable salts thereof, said compound being administered in an effective amount to increase the bile flow and reduce the lipid level in said system.

2. The method of claim 1 wherein said compound is 3α, 12α-dihydroxy-etiocholane-17β-carboxylic acid.

3. The method of claim 1 wherein said compound is 3α, 12α-dihydroxy-5 β-23,24-bisnorcholanic acid.

4. The method of claim 1 wherein said compound is administered in an amount of from 0.1 to 30 mg/kg per day.

5. A method of reducing increasing the bile flow in mammals comprising administering to mammals, in amount sufficient to increase bile flow, a compound of the formula

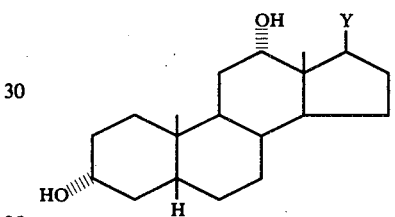

wherein Y is —C—OH;

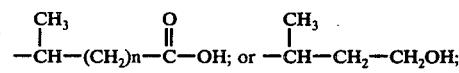

and n is an integer of from 0 to 1; or pharmaceutically acceptable salts thereof.

6. The method of claim 5 wherein said compound is 3α, 12α-dihydroxy-etiocholane-17β-carboxylic acid.

7. The method of claim 5 wherein said compound is 3α, 12α-dihydroxy-5β-23,24-bisnorcholanic acid.

8. The method of claim 5 wherein said compound is administered in an amount of from 0.1 to 30 mg/kg per day.

9. A method of reducing cholesterol levels in the blood stream of mammals comprising administering to said system in an amount sufficient to reduce the cholesterol levels a compound of the formula

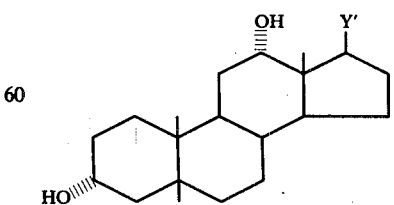

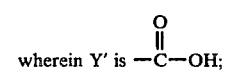

-continued

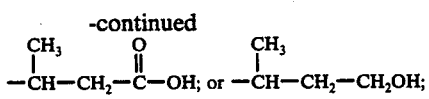

or pharmaceutically acceptable salts thereof.

10. The method of claim 9 wherein said compound is 3α, 12α-dihydroxy-etiocholane-17β-carboxylic acid.

11. The method of claim 9 wherein said compound is administered to an amount of from 0.1 to 30 mg/kg per day.

12. The method of claim 9 wherein said compound is 3α, 12α-dihydroxy-5β-norcholanic acid.

13. The method of claim 9 wherein said compound is 3α, 12α, 23-trihydroxy-5β-24-norcholane.

14. A method of reducing the triglyceride levels in the blood stream of mammals comprising administering to mammals in an amount sufficient to reduce the cholesterol levels a compound of the formula

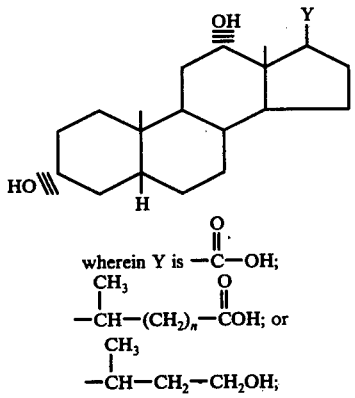

wherein Y is —C(=O)—OH;
—CH(CH₃)—(CH₂)ₙ—COH; or
—CH(CH₃)—CH₂—CH₂OH;

and $n$ is an integer of from 0 to 1 or pharmaceutically acceptable salts thereof.

15. The method of claim 14 wherein said compound is 3α, 12α-dihydroxy-etiocholane-17β-carboxylic acid.

16. The method of claim 14 wherein said compound is 3α, 12α-dihydroxy-5β-23,24-bisnorcholanic acid.

17. The method of claim 14 wherein said compound is administered in an amount of from 0.1 to 30 mg/kg per day.

18. The process of claim 14 wherein said compound is 3α, 12α-dihydroxy-5β-norcholanic acid.

19. The process of claim 14 wherein said compound is 3α, 12α, 23-trihydroxy-5β-24-norcholane.

20. A composition useful for increasing the bile flow while simultaneously reducing lipid levels comprising a pharmaceutically acceptable carrier and an effective amount of compound of the formula

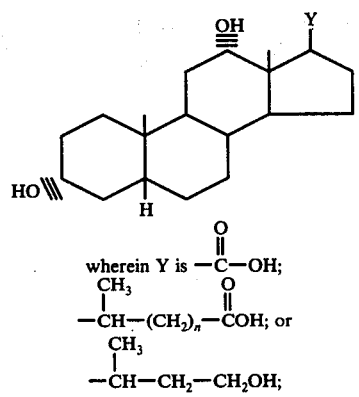

wherein Y is —C(=O)—OH;
—CH(CH₃)—(CH₂)ₙ—COH; or
—CH(CH₃)—CH₂—CH₂OH;

and $n$ is an integer from 0 to 1 or pharmaceutically acceptable salts thereof.

21. The composition of claim 17 wherein said compound is 3α, 12α-dihydroxy-etiocholane-17β-carboxylic acid.

22. The composition of claim 17 wherein said compound is 3α, 12α-dihydroxy-5β-23,24-bisnorcholanic acid.

23. The composition of claim 17 wherein said compound is 3α, 12α-dihydroxy-5β-norcholanic acid.

* * * * *